United States Patent [19]

Mott

[11] 4,078,431
[45] Mar. 14, 1978

[54] ENTHALPY CALCULATOR

[75] Inventor: Richard C. Mott, Harwood Heights, Ill.

[73] Assignee: Honeywell Inc., Minneapolis, Minn.

[21] Appl. No.: 743,427

[22] Filed: Nov. 19, 1976

[51] Int. Cl.² .......................................... G01K 17/00
[52] U.S. Cl. ...................................... 73/336; 73/344
[58] Field of Search ............... 73/29, 190 R, 336, 344; 235/151.3; 236/44 C

[56] References Cited
U.S. PATENT DOCUMENTS 3,521,488  7/1970  Preiser et al. ......................... 73/336
3,681,992  11/1969  Cofold et al. ......................... 73/336

FOREIGN PATENT DOCUMENTS 760,668  11/1956  United Kingdom .................. 73/336

Primary Examiner—Herbert Goldstein
Attorney, Agent, or Firm—Trevor B. Joike

[57] ABSTRACT

An enthalpy calculator is disclosed having a humidity sensor for sensing relative humidity, connected to a multiplier and a temperature sensor, for sensing temperature, also connected to the multiplier wherein the output of the multiplier provides a signal which is representative of enthalpy. The multiplier may be a variable gain amplifier with the temperature sensor and humidity sensor connected to the input and in the feedback loop in either order such that either the temperature sensor or the humidity sensor changes the gain of the amplifier.

11 Claims, 3 Drawing Figures

ENTHALPY CALCULATOR

BACKGROUND OF THE INVENTION

This invention relates to a device for providing a signal which is representative of enthalpy and is particularly directed to a device for combining temperature and relative humidity to produce this signal representative of enthalpy.

In the control of air conditioning and heating systems, it has long been desired to use enthalpy, particularly in those systems which must choose the portion of return air and the portion of outdoor air to be treated and then supplied to the zones under the control of the system. For example, during the air conditioning or summer season, it is desirable to bring in a large portion of outdoor air when the outdoor air is cool and dry. If the outdoor air is cool but humid, it may be desirable to increase the portion of return air mixed with the outdoor air to reduce the amount of dehumidification necessary to provide comfortable conditions. Similarly, if the outdoor air is warm but relatively dry, it still may be advantageous to increase the portion of return air mixed with the outdoor air to maintain at a minimum the amount of energy expended to cool this air to within the comfortable range. And, of course, if the outdoor air is both warm and humid, the amount of energy needed to cool and dehumidify this air is substantial and, therefore, the portion of return air is increased and the portion of outdoor air is decreased.

Various prior art arrangements have been used to provide this type of control. Some of these arrangements measure only outdoor air temperature and return air temperature which merely gives an indication of the sensible heat content of the air that is being measured. Total heat (specific heat content plus latent heat content), however, is a better measurement of how much temperature and humidity treatment is necessary to provide comfortable conditions since specific heat content measurement along ignores the moisture content of the air being controlled. It is therefore necessary to measure the latent heat content of the air as well.

In order to measure the total heat content (i.e. latent heat plus sensible heat) of air, prior art arrangements measured both the temperature and humidity of the outdoor air as well as the temperature and humidity of the indoor air. Such a system, however, must rely upon four sensors for providing this measurement of total heat, i.e. enthalpy. The use of humidity and temperature sensors have been in very complex circuit arrangements in order to give a reasonable approximation of total heat or they have been used together with computer programs for calculating enthalpy according to the prescribed enthalpy formula. In order to reduce the number of sensors required to measure this total heat or enthalpy, the prior art systems utilized wet bulb temperature sensors which, if one reviews the psychometric chart, gives a fairly accurate indication of total heat or enthalpy. However, wet bulb temperature sensors are complex and require a constant source of water. Applicant has devised a system for giving a reasonably accurate approximation of enthalpy relying upon a simple circuit having a humidity input and a temperature input.

SUMMARY OF THE INVENTION

This circuit multiplies both humidity and temperature together according to an approximation formula to provide an output dependent or representative of enthalpy. More specifically, the humidity sensor is connected in the primary loop of an amplifier and the temperature sensor is connected in the feedback loop to provide the multiplication function and produce a signal representative of enthalpy. The sensors may be reversed with a corresponding adjustment of circuit values. Such an arrangement can be done fluidically, such as pneumatically, or electrically.

BRIEF DESCRIPTION OF THE DRAWINGS

These and other features and advantages will become apparent from a detailed consideration of the drawings in which.

DETAILED CONSIDERATION OF THE INVENTION

Figure 1:
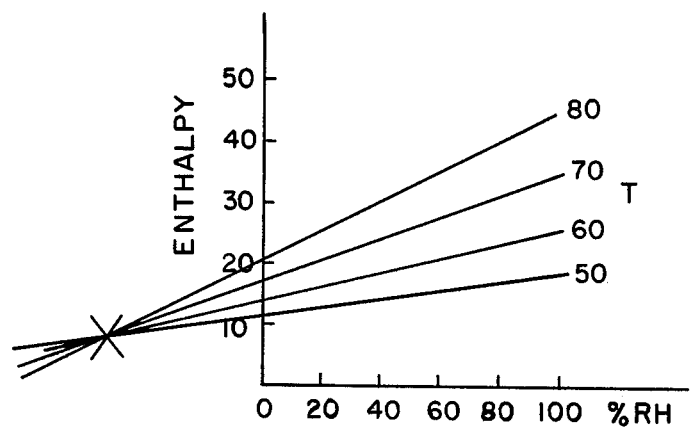
FIG. 1 shows the enthalpy curves based on temperature and relative humidity which can be derived from the psychometric chart.

A review of the psychometric chart will reveal that enthalpy is linearly related to relative humidity at a constant dry bulb temperature. In FIG. 1, enthalpy has been shown as a function of relative humidity for specified dry bulb temperatures. This graph can be easily made from the psychometric chart by following the constant dry bulb temperature lines and plotting the enthalpy versus relative humidity points. As can be seen from FIG. 1, the enthalpy lines are linear. This review also reveals that, for a small range of dry bulb temperatures, there is a nearly common intersection point for the plots of relative humidity versus enthalpy for various dry bulb temperatures. This intersection point is shown as an "X" in FIG. 1.

Given this information, it is possible to express enthalpy as follows:

$$H = 8 + (0.00493T - 0.17)(RH + 50),$$

where $H$ = enthalpy, $T$ = dry bulb temperature, and $RH$ = relative humidity. This formula is an approximation since the intersection point is not common to all of the enthalpy plots shown in FIG. 1 but is nearly common to all. As can be seen from this formula, enthalpy is dependent upon the multiplication of the dry bulb temperature and relative humidity. Therefore, circuits, both pneumatic and electric, can be provided for producing an output signal representative of enthalpy based upon both temperature and humidity.

Figure 2:
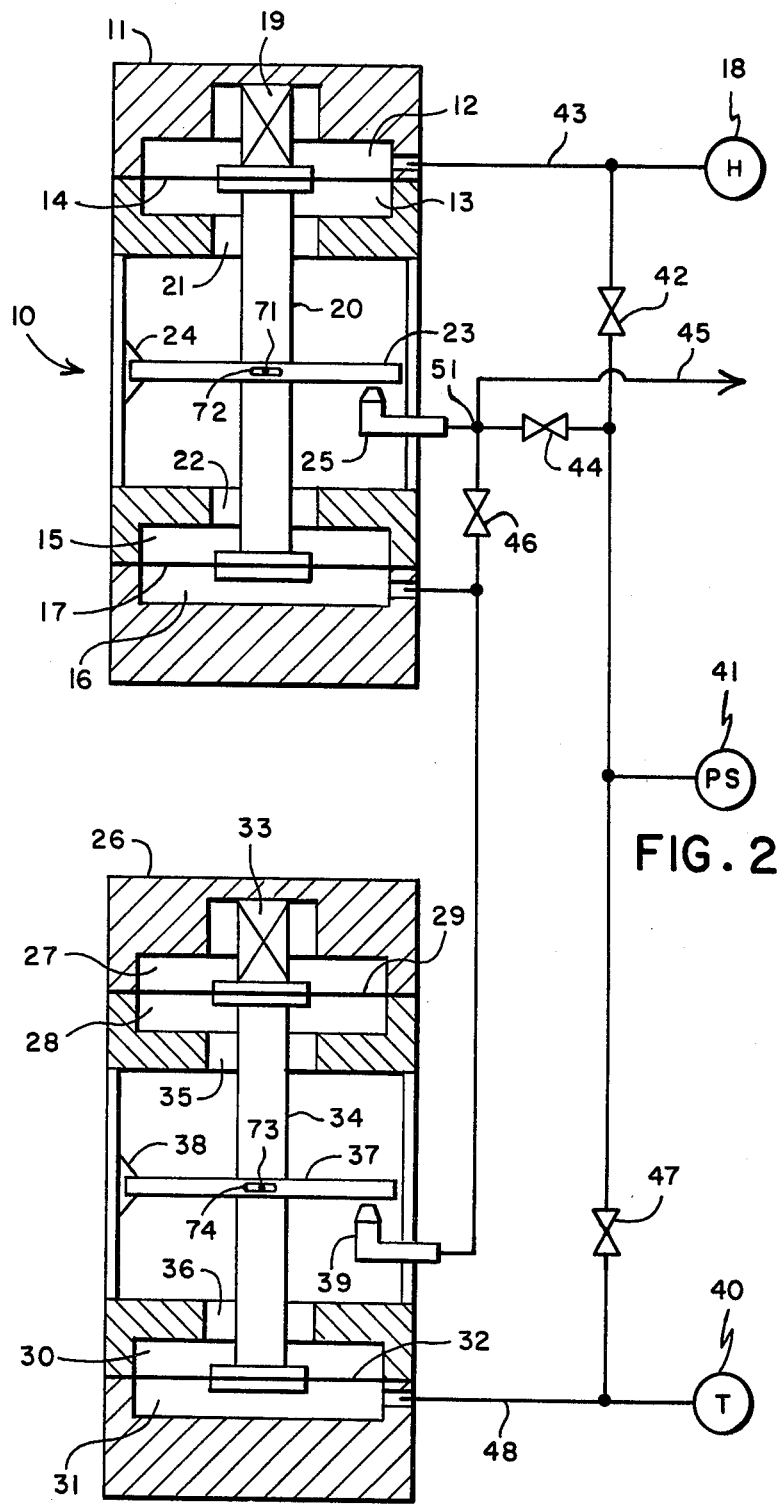
FIG. 2 shows a pneumatic arrangement for relying on both relative humidity and temperature to produce a signal representative of enthalpy.

A pneumatic circuit relying upon this formula is shown in FIG. 2. A variable gain amplifier 10 has a housing 11 divided into first and second chambers 12 and 13 by a diaphragm 14 and third and fourth chambers 15 and 16 divided by a diaphragm 17. Chamber 12 is connected to a humidity sensor 18 and has therein a spring 19 which, as one skilled in the art will readily recognize, can be made adjustable by any suitable means. The spring 19 and the pressure supplied by the humidity sensor 19 act downwardly on the diaphragm 14. A force transmitter 20 connects diaphragm 14 to diaphragm 17. Chambers 13 and 15 are connected to atmosphere through suitable vents 21 and 22. Connected pivotally by pin 71 and slot 72 to the force transmitter is a lever 23 also pivotally connected to the housing 11 at 24. The lever 23 acts in conjunction with a nozzle 25. A second housing 26 has a first chamber 27 and a second chamber 28 divided by a diaphragm 29 and a third chamber 30 and fourth chamber 31 divided by a diaphragm 32. A spring 33 is contained within the chamber 27 for providing a downward biasing force on the diaphragm 29. Again, as one skilled in the art will readily recognize, the spring 33 can easily be made adjustable. A force transmitter 34 connects the diaphragm 29 to the diaphragm 32 and chambers 28 and 30 are connected to atmosphere through vents 35 and 36. Pivotally connected by pin 73 and slot 74 to the force transmitter 34 is a lever 37 also pivotally connected to the housing 26 at 38. The lever 37 cooperates with a nozzle 39. Chamber 31 is connected to a temperature sensor 40 which provides a pressure within chamber 31 dependent upon temperature. This pressure acts upwardly on diaphragm 32.

A main source or supply source of pressure 41 is connected through a restriction 42 to supply pressure to the humidity sensor 18. Humidity sensor 18 may be a bleed type humidity sensor for controlling the pressure in line 43 to the chamber 12. Supply source 41 is also connected through a restriction 44 to the nozzle 25 and an output line 45 is also connected to the nozzle 45. The nozzle 25 is further connected through a restriction 46 to the chamber 16 and the junction of restriction 46 and chamber 16 is connected to the nozzle 39. Source 41 is further connected through a restriction 47 to the temperature sensor 40 which may be a bleed type temperature sensor for controlling the pressure in line 48 to the chamber 31.

The diaphragm unit or module defined by housing 26 acts as a variable feedback means which is controlled by the temperature sensor 40. Diaphragm module 10 is a variable gain amplifer as above mentioned. Any change in humidity will result in a change of the pressure in the chamber 12 which will result in movement of the force transmitter 20 and change the position of lever 23 with respect to nozzle 25. This change of position of the lever 23 with respect to the nozzle 25 will result in a change of the pressure at point 51 which is connected both to the chamber 16, which acts as a feedback chamber, and to the nozzle 39 through restriction 46. The pressure in nozzle 39 is also controlled by the position of the lever 37 with respect to the nozzle 39. The position of the lever 39 is controlled by force transmitter 34 which is in turn controlled by the pressure output of the temperature sensor 40. Thus, any change in temperature will result in a change in the pressure output from nozzle 39 which affects the feedback pressure from nozzle 25 to the feedback chamber 16. Thus, any resultant change in the humidity as sensed by the humidity sensor 18 or temperature as sensed by the temperature sensor 40 will result in a change of the output on line 45. By controlling the size of the various diaphragms and of the springs, the arrangement shown in FIG. 2 can be made to operate according to the formula above mentioned. As such, the output on line 45 will represent the enthalpy of the body of air or gas to which the humidity sensor 18 and the temperature sensor 40 are exposed.

Figure 3:
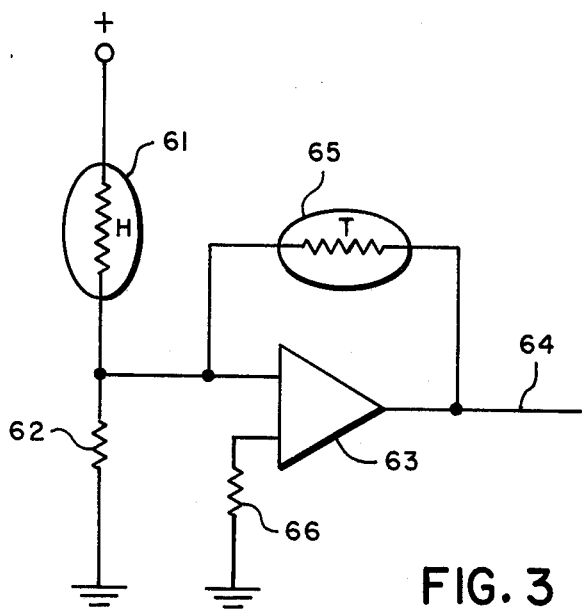
FIG. 3 shows an electronic system for combining temperature and humidity to produce enthalpy.

FIG. 3 shows an electric circuit for providing an output representative of enthalpy dependent upon both humidity and temperature. Humidity sensor 61 is connected from a positive source to ground through a resistor 62. The common junction of the humidity sensor 61 and resistor 62 is connected to one input of variable gain amplifier 63 which has an output 64. The output of amplifier 64 is connected back to the input to which the humidity sensor 61 is connected through a temperature sensor 65. The other input of amplifier 63 is connected by a resistor 66 to ground. The amplifier 63 provides the multiplication function defined by the above mentioned formula. By properly sizing the various elements including the resistors 62 and 66 according to this formula, the output from the amplifier 63 on line 64 is representative of enthalpy based upon the humidity sensed by humidity sensor 61 and the temperature sensed by temperature sensor 65.

It is apparent that certain modifications of the invention can be made with departing from the scope thereof, and, therefore, the scope of the invention is to be limited only by the appended claims.

The embodiments of the invention in which an exclusive property or right is claimed are defined as follows:

1. An enthalpy calculator for calculating the enthalpy of a body of gas based upon the temperature and relative humidity of said gas comprising:
   humidity sensing means for producing a signal dependent upon said relative humidity;
   temperature sensing means for producing a signal dependent upon said temperature; and
   multiplier means connected to both said humidity sensing means and said temperature sensing means multiplying said signal dependent upon said relative humidity and said signal dependent upon said temperature in a manner to produce an output representative of the enthalpy of said gas.

2. The enthalpy calculator of claim 1 wherein said multiplier means comprises variable gain means having input means, output means and a gain capable of being varied, first connecting means connecting one of said humidity sensing means and said temperature sensing means to said input means, and second connecting means including feedback means connecting the other of said humidity sensing means and said temperature sensing means to said input means and to said output means.

3. The enthalpy calculator of claim 2 wherein said variable gain means comprises a variable gain amplifier.

4. The enthalpy calculator of claim 3 wherein said first connecting means connects said humidity sensing means to said input means and said second connecting means connects said temperature sensing means to said input means and to said output means.

5. The enthalpy calculator of claim 4 wherein said variable gain amplifier comprises a pneumatic diaphragm module having a housing, said input means comprising first and second chambers of said housing, said first connecting means connecting said humidity sensing means to a source of supply of pressure and to said first chamber for supplying to said first chamber said relative humidity dependent signal in the form of a pressure, and said second connecting means including said feedback means connecting said temperature sensing means to said source of supply of pressure to said second chamber and to said output means for supplying to said second chamber said temperature dependent signal and a feedback signal dependent upon said output.

6. The enthalpy calculator of claim 5 wherein said feedback means comprises a pneumatic diaphragm module having a housing, said housing of said feedback means having a third chamber and an output means, and said second connecting means connecting said temperature sensing means to said source of supply pressure and to said third chamber for supplying to said third chamber a pressure dependent upon said temperature, said output means of said housing of said feedback means generating said temperature dependent signal to said second chamber of said pneumatic diaphragm module of said variable gain amplifier.

7. The enthalpy calculator of claim 6 wherein said output means of said variable gain amplifier comprises force transmitting means responsive to the pressure in said first and second chambers of said pneumatic diaphragm modules of said variable gain amplifier, a lever responsive to said force transmitting means and a nozzle responsive to movement of said lever and connected to said source of supply pressure, to said second chamber of said diaphragm module of said variable gain amplifier and to an output line for providing said output representative of enthalpy, and wherein said output means of said pneumatic diaphragm module of said feedback means comprises a force transmitter responsive to said pressure in said third chamber, a lever responsive to said force transmitting means and a nozzle responsive to said lever connected to said second chamber of said diaphragm module of said variable gain amplifier means.

8. The enthalpy calculator of claim 7 wherein said first connecting means comprises a first pneumatic line connecting said humidity sensing means to said first chamber of said pneumatic diaphragm module of said variable gain amplifier and second pneumatic line including a restriction connecting said humidity sensing means to said source of supply pressure.

9. The enthalpy calculator of claim 7 wherein said second connecting means comprises a pneumatic line connecting said temperature sensing means to said third chamber, a pneumatic line having a restriction connecting said temperature sensing means to said source of supply pressure, a pneumatic line connecting said nozzle of said pneumatic diaphragm module of said feedback means to said second chamber of said pneumatic diaphragm module of said variable gain amplifier, a pneumatic line having a restriction connecting said second chamber of said pneumatic diaphragm module of said variable gain amplifier to said nozzle of said pneumatic diaphragm module of said variable gain amplifier, a pneumatic line including a restriction connecting said nozzle of said pneumatic diaphragm of said variable gain amplifier to said source of supply pressure and an output line connected to said nozzle of said pneumatic diaphragm module of said variable gain amplifier for providing said output representative of enthalpy.

10. The enthalpy calculator of claim 4 wherein said variable gain amplifier comprises an electronic variable gain amplifier wherein said first connecting means comprises resistor means connecting said humidity sensing means from a source of potential to a reference source of potential and to said input means of said variable gain amplifier, said second connecting means comprises means connecting said temperature sensing means from said output means of said amplifier to said input means, and wherein said variable gain amplifier has second input means connected by resistor means to a second reference level wherein said output means provides an output representative of enthalpy.

11. An enthalpy calculator for calculating the enthalpy, H, of a body of gas based upon the temperature and humidity of said gas comprising:

humidity sensing means for producing a signal RH dependent upon said humidity;

temperature sensing means for producing a signal T dependent upon said humidity; and, means connected to said humidity sensing means and to said temperature sensing means for providing an output representative of said enthalpy, H, substantially in accordance with the formula $$H = 8 + (0.00493T - 0.17)(RH + 50).$$

* * * * *